United States Patent
Eckhardt et al.

(10) Patent No.: US 6,613,437 B1
(45) Date of Patent: Sep. 2, 2003

(54) TWO-COMPONENT PREPARATIONS CONTAINING EPOXY COMPOUNDS

(75) Inventors: Gunther Eckhardt, Bad Duerrenberg (DE); Bernd Gangnus, Andechs (DE); Wolfgang Weinmann, Gilching (DE); Cornelia Fuehrer, Herrsching (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 09/936,822

(22) PCT Filed: Mar. 17, 2000

(86) PCT No.: PCT/EP00/02388

§ 371 (c)(1),
(2), (4) Date: Nov. 28, 2001

(87) PCT Pub. No.: WO00/56800

PCT Pub. Date: Sep. 28, 2000

(30) Foreign Application Priority Data

Mar. 18, 1999 (DE) .......................... 199 12 251

(51) Int. Cl.[7] .............................. B32B 27/38
(52) U.S. Cl. ............... 428/413; 424/423; 433/222.1; 433/228.1; 433/229; 428/414; 523/455; 528/98
(58) Field of Search .............. 523/455; 528/98; 428/413, 414; 433/222.1, 228.1, 229; 424/423

(56) References Cited

U.S. PATENT DOCUMENTS

| | | |
|---|---|---|
| 5,494,943 A | 2/1996 | Mahoney et al. |
| 5,556,896 A | 9/1996 | Hyerley et al. |
| 5,672,637 A | 9/1997 | Mahoney et al. |
| 6,245,828 B1 * | 6/2001 | Weinmann et al. ......... 522/148 |

FOREIGN PATENT DOCUMENTS

| | | |
|---|---|---|
| DE | A1-4324322 | 1/1995 |
| DE | U1-9420158.7 | 3/1995 |
| DE | A1-19502751 | 8/1996 |
| DE | A1-19648283 | 5/1998 |
| DE | A1-19742980 | 1/1999 |
| DE | A1-19753461 | 6/1999 |
| EP | A2688804 | 12/1995 |
| EP | A2764691 | 3/1997 |
| JP | A4175303 | 6/1992 |
| WO | A2-9613538 | 5/1996 |

* cited by examiner

Primary Examiner—Robert Dawson
Assistant Examiner—D. Aylward
(74) Attorney, Agent, or Firm—Birch Stewart Kolasch & Birch LLP

(57) ABSTRACT

The invention relates to two-component preparations comprising components (I) and (II), wherein at least one component comprises epoxy compounds and the preparations cure by cationic polymerization, initiated by Lewis and/or Brönsted acids, after mixing of the two components, the preparations comprising the Lewis and/or Brönsted acids in the form of precursor compounds which are suitable for the formation of Lewis and/or Brönsted acids.

20 Claims, No Drawings

TWO-COMPONENT PREPARATIONS CONTAINING EPOXY COMPOUNDS

This application is the national phase under 35 U.S.C. §371 of PCT International Application No. PCT/EP00/02388 which has an International filing date of Mar. 17, 2000, which designated the United States of America.

The invention relates to two-component preparations comprising epoxy compounds, in particular for the preparation of dental compositions. The invention particularly relates to two-component dental compositions which comprise epoxy compounds and are cured by cationic polymerization.

An important parameter of multi-component dental compositions is their processing time. This is understood as meaning the time from the start of setting after mixing of the component to curing of the composition. After mixing the components of the dental composition, the user requires an exactly defined period of time in which he can handle the composition without problems. Directly after this period of time the composition should harden within the shortest time. A slow solidifying of the composition during processing or working is intolerable for the user.

Various systems which attempt to adjust the course of setting of a curing dental composition are known from the prior art.

DE-A-197 53 461 describes, for example, storage-stable cationically polymerizing preparations in which soluble and/or finely divided alkaline earth metal and/or alkali metal compounds allow adjustment of the course of setting. In the case of two-component formulations, the initiator system described there can comprise, inter alia, free Lewis or Brönsted acids. A disadvantage of these preparations is that they allow only a very limited period of time for adjustment of the start of setting, and in addition if the concentration of alkaline earth or alkali metals is increased for the purpose of extending the setting range, they severely delay the end of setting and severely adversely impair the mechanical properties.

DE-A-197 42 980 indeed describes in principle cationically polymerizable compositions, but these are based on ROMP oligomers or polymers, it being possible for epoxy-functional comonomers to be added to the compositions. Free Lewis or Brönsted acids are employed in the catalyst system mentioned. A disadvantage of this system is the fact that the course of setting cannot be adjusted. After the start of the polymerization, this starts to proceed and leads to a hard material with a low volume shrinkage within an extremely short time.

DE-A-195 02 751 describes photocurable model materials for dentistry in which Lewis acids can be formed by a suitable light source. Photocurable materials indeed in principle have a processing time of any desired length, but in practice this property would take effect only in a dark room. In the dental sector, however, work is carried out in without protection in daylight or under an intense artificial light source, which lead to a gradual solidifying of the dental material, as a result of which these initiation systems are not suitable for the preparation of dental materials with a widely adjustable processing time.

Further polymerizable compositions based on epoxides with Lewis or Brönsted acids in free or reactive form as the catalyst or initiator system are known from DE-A-196 48 283. A disadvantage of these compositions in turn is that the setting characteristics cannot be adjusted.

The invention is based on the object of providing dental compositions which do not have the disadvantages from the prior art.

This object is achieved by two-component preparations, wherein at least one component comprises epoxy compounds and the preparations cure by cationic polymerization, initiated by Lewis and/or Brönsted acids, after mixing of the two components, the preparations comprising the Lewis and/or Brönsted acids in the form of precursor compounds which are suitable for the formation of Lewis and/or Brönsted acids and which are formed by chemical reaction during or after mixing of the components.

The advantages of the dental compositions prepared from the preparations according to the invention lie in the exact adjustability of the processing time and in the outstanding physical values of the cured dental compositions.

In particular, when the dental compositions are used as model materials in dentistry for the production of working models, further advantages are found: Compared with gypsum, the compositions according to the invention show increased mechanical values, such as abrasion resistance, tensile strength and compressive strength. The detail reproduction of fine contours and grooves and the dimensional accuracy, which is largely influenced by the lowest possible polymerization shrinkage, are also considerably better. Compared with model materials known to date which are based on plastics and are distinguished by a rather cumbersome handling and/or by too long a setting phase compared with gypsum, the dental compositions according to the invention can be mixed automatically and the setting phase can be adjusted in an outstanding manner. The end of the setting phase determines the earliest possible point in time at which the model can be removed from the mould and worked further.

The preparations are also suitable for other dental applications where low shrinkage is an advantage, for example as materials for the production of temporary crowns and bridges and fixing cements.

The preparations according to the invention comprise two components (I) and (II).

The epoxy compounds and the Lewis and/or Brönsted acids in the form of compounds which are capable of the formation of Lewis and/or Brönsted acids and do not react with the epoxy compounds can be present in component (I) and/or in component (II) in any desired distribution.

Dental compositions obtained from the preparations according to the invention comprise, distributed over components (I) and (II), the following constituents:

(A) 10 to 80 wt. %, preferably 10 to 60 wt. %, of epoxy compounds, (B) 0.01 to 20 wt. %, preferably 0.1 to 10 wt. %, of compounds which are capable of formation of Lewis or Brönsted acids, and optionally free Lewis and/or Brönsted acids, (C) 10 to 89.99 wt. %, preferably 30 to 89.99 wt. %, of diluents, (D) 0 to 79.99 wt. %, preferably 15 to 59.99 wt. %, of modifiers.

Epoxy compounds according to constituent (A) can be cycloaliphatic and/or aromatic and/or aliphatic epoxy compounds with at least two and/or at least four epoxy groups.

Cycloaliphatic epoxides can be, for example, the epoxides known from DE-A-196 48 283, which correspond to the following general formulae:

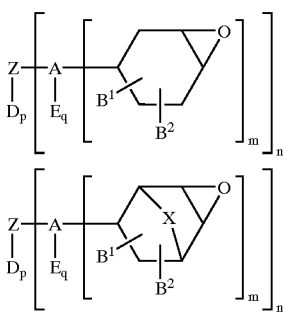

in which the symbols have the following meanings:

Z an aliphatic, cycloaliphatic or aromatic radical having 0 to 22, preferably 0 to 18 C atoms, or a combination of these radicals, it being possible for one or more C atoms to be replaced by O, C=O, —O(C=O)—, $SiR_2$ and/or NR, wherein R is an aliphatic radical having 1 to 7 C atoms, it being possible for one or more C atoms to be replaced by O, C=O and/or —O(C=O)—, A an aliphatic, cycloaliphatic or aromatic radical having 1 to 18, preferably 1 to 15 C atoms or a combination of these radicals, it being possible for one or more C atoms to be replaced by O, C=O, —O(C=O)—, $SiR_2$ and/or NR, wherein R is an aliphatic radical having 1 to 7 C atoms, in which one or more C atoms can be replaced by O, C=O and/or —O(C=O)—, $B^1$, $B^2$, D, E independently of one another, an H atom or an aliphatic radical having 1 to 9, preferably 1 to 7 C atoms, it being possible for one or more C atoms to be replaced by O, C=O, —O(C=O)—, $SiR_2$ and/or NR, wherein R is an aliphatic radical having 1 to 7 C atoms, in which one or more C atoms can be replaced by O, C=O and/or =O(C=O)—, X $CH_2$, S or O, n 2 to 7, preferably 2 to 5, m 1 to 10, preferably 1 to 7, p 1 to 5, preferably 1 to 4, and q 1 to 5, preferably 1 to 4.

Low-viscosity epoxides such as are described in DE-A-196 48 283 can also be employed.

The epoxides known from U.S. Pat. Nos. 2,716,123, 2,985,667, 2,750,395, 2,863,881, 3,187,018, 5,085,124, EP-A-0 449 027 and EP-A-0 574 265 are also suitable, in particular epoxides of the following structural formulae

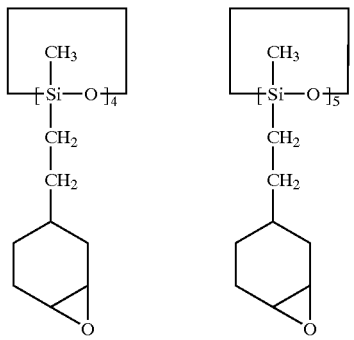

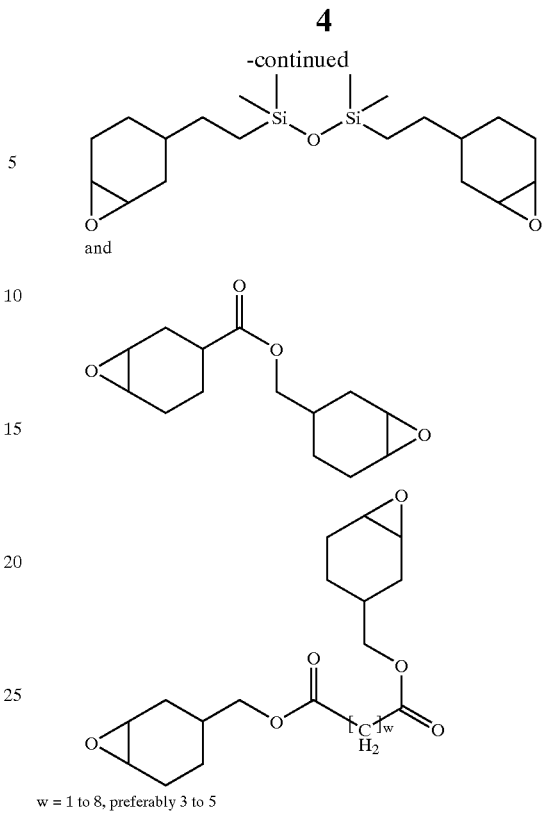

w = 1 to 8, preferably 3 to 5

Combinations of aliphatic, cycloaliphatic or aromatic epoxides are possible. Cycloaliphatic epoxy compounds with at least two epoxy groups, cycloaliphatic epoxy compounds with at least four epoxy groups or the combination of cycloaliphatic epoxy compounds with two epoxy groups and cycloaliphatic epoxy compounds with at least four epoxy groups are preferably employed.

The Lewis and/or Brönsted acids according to constituent (B) are formed by chemical reactions of selected constituents of the two components during or after mixing thereof. Free Lewis and/or Brönsted acids such as are known from conventional systems can also be employed.

In the case where free Lewis or Brönsted acids are additionally used, it has proved expedient to add the acids to that component which comprises no epoxy compounds. Where appropriate, to adjust the processing time it is expedient also to employ the substances for delaying cationic polymerization known from DE-A-197 53 461—which has not yet been published at the time of this Application.

Examples of free acids which may be mentioned are: $BF_3$ or adducts thereof, such as, for example, $BF_3 \exists THF$, $BF_3 \exists Et_2O$, $AlCl_3$, $FeCl_3$, $HPF_6$, $HAsF_6$, $HSbF_6$ and $HBF_4$.

Both components of the dental compositions according to the invention can additionally comprise certain contents of so-called photoinitiators which form Brönsted or Lewis acids when irradiated with light of the wavelength range from 200 to 650 nm. Typical classes of compounds for these photoinitiators are onium salts, such as diazonium, sulphonium, iodonium and ferrocenium salts with complex anions of low nucleophilicity. These include, for example, diazonium compounds (U.S. Pat. No. 3,205,157), sulphonium compounds (U.S. Pat. No. 4,173,476) and iodonium compounds (U.S. Pat. Nos. 4,264,703, 4,394,493). In the examples mentioned, instructions are given to use ultraviolet light.

Derivatives of cyclopentadienyl-iron-arene complexes (EP-A-0 094 915, WO-96/03453, EP-A-0 661 324) can also be used. It is also possible to add α-dicarbonyl compounds, for example camphorquinone, which act as sensitizers in the visible range. Combined preparations of camphorquinone and iodonium compounds are known from U.S. Pat. Nos. 5,554,676 and 4,828,583.

To produce the Brönsted and/or Lewis acids, the components comprising photoinitiators are irradiated, before mixing, by lamps which emit light of the required wavelength range.

The photoinitiators are preferably employed in a component which comprises no epoxy compounds.

The Brönsted and/or Lewis acids are produced by selected constituents which are stored separately in the two components and which react chemically with one another during or after mixing of the two components.

Typical examples of those reactions which can lead to the acids necessary for initiation of the polymerization of epoxy compounds are redox reactions using bisaryliodonium salts, reducing agents and copper complexes, and the dehalogenation of alkyl halides assisted by metal salts.

In the case of these latent initiation systems, it is possible to add the particular reaction partner both to the components comprising epoxy compounds and to the component which comprises no epoxy compounds.

In general, the distribution of the constituents of the latent initiation systems over the two components is undertaken such that premature polymerization of the epoxy compounds during storage of the two-component materials is reliably avoided.

This object is achieved, for example, by using components which cannot be polymerized by acids and which comprise the particularly critical constituent of the particular latent initiation system.

In the case of the formation of acids by redox reactions from bisaryliodonium salts, reducing agents and copper compounds, for example, it has thus proved expedient to store the bisaryliodonium salts and the reducing agents in a component which comprises no epoxy compounds. A further component then comprises the copper compounds together with the epoxy compounds.

The iodonium salts are present in the components to the extent of 0.01 to 20 wt. %, preferably 0.2 to 10 wt. %, based on the weight of the mixed material, the reducing agents also necessary are present to the extent of 0.01 to 10 wt. %, preferably 0.05 to 5 wt. %, based on the weight of the mixed material, and the copper compounds are present to the extent of 0.005 to 10 wt. %, preferably 0.01 to 5 wt. %, based on the weight of the mixed material.

The bisaryliodonium compounds, for example, which are known from U.S. Pat. Nos. 4,225,691 and 4,238,587 are suitable. Methods for the preparation of further diaryliodonium compounds are known from F. M. Beringer, R. A. Falk, M. Karmal, J. Lillien, G. Masullo, M. Mausner, E. Sommers, J. Am. Chem. Soc., 81, 342 (1958) and I. Mason, Nature, 139, 150 (1937).

Diaryliodonium compounds, which are known, inter alia, from DE-A-197 36 471, are particularly preferred. They have the following structure:

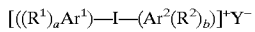

$Ar^1$ and $Ar^2$ independently of one another can be different, substituted or unsubstituted, fused or non-fused aromatic systems having 4 to 20 C atoms, such as, for example, phenyl, tolyl, cumyl, anisyl, chlorophenyl, nitrophenyl, naphthyl, thienyl, furanyl and pyrazolyl, wherein $R^1$ and $R^2$ are identical or different and independently of one another denote an H atom, an aliphatic radical having 1 to 19, preferably 1 to 9 C atoms, it being possible for one or more C atoms to be replaced by O, C=O, —O(C=O)—, F, Cl, Br, $SiR^3_3$ and/or $NR^3_2$, wherein $R^3$ is an aliphatic radical having 1 to 7 C atoms, in which one or more C atoms can be replaced by O, C=O and/or —O(C=O)—, and a and b independently of one another can be 1 to 5. The aromatics $Ar^1$ and $Ar^2$ can be bonded to one another via $R^1$ and/or $R^2$.

The counter-anion $Y^-$ is an anion of low nucleophilicity of the following structure:

wherein K is an element of main group IIII, V or VII, such as B, Al, P, Sb, As or I, and x can assume numerical values from 1 to 4. The L independently of one another denote aromatic, aliphatic, araliphatic or cycloaliphatic radicals having 1 to 25 C atoms, in which one or more C atoms can be substituted by F, Cl, Br or I, and y can assume numerical values from 0 to 6.

Preferred radicals L are pentafluorophenyl, tetrafluorophenyl, trifluorophenyl, fluorophenyl, phenyl, 4-trifluoromethylphenyl, 3,5-bis(trifluoromethyl)phenyl, 2,4,6-tris(trifluoromethyl)phenyl, fluorine and iodine.

Particularly preferred counter-anions $Y^-$ are $PF_6^-$, $AsF_6^-$, $SbF_6^-$, $B(C_6F_5)_4^-$ and $BF_4^-$.

Further diaryliodonium compounds are also described, for example, in U.S. Pat. No. 4,246,703.

Particularly suitable diaryliodonium compounds are:

diphenyliodonium tetrafluoroborate
diphenyliodonium hexafluorophosphate
diphenyliodonium hexafluoroantimonate
diphenyliodonium tetrakis(pentafluorophenyl)borate
bis-(4-methylphenyl)iodonium hexafluorophosphate
bis-(4-methylphenyl)iodonium hexafluoroantimonate
bis-(4-methylphenyl)iodonium tetrakis(pentafluorophenyl)borate
phenyl-4-methylphenyliodonium hexafluorophosphate
phenyl-4-methylphenyliodonium hexafluoroantimonate
phenyl-4-methylphenyliodonium tetrakis(pentafluorophenyl)borate
phenyl-4-methoxyphenyliodonium hexafluoroantimonate
phenyl-4-methoxyphenyliodonium tetrakis(pentafluorophenyl)borate
phenyl-3-nitrophenyliodonium hexafluorophenylantimonate
phenyl-3-nitrophenyliodonium tetrakis(pentafluorophenyl)borate
bis(4-tert-butylphenyl)iodonium hexafluoroantimonate
bis(4-tert-butylphenyl)iodonium tetrakis(pentafluorophenyl)borate
phenyl-4-diphenyliodoinium hexafluoroantimonate
dinaphthyliodonium hexafluorophosphate
dinaphthyliodonium hexafluoroantimonate
dinaphthyliodonium tetrakis(pentafluorophenyl)borate
bis(4-dodecylphenyl)iodonium hexafluoroantimonate
bis(4-dodecylphenyl) tetrakis(pentafluorophenyl)borate
4-methylphenyl-4-isopropylphenyliodonium hexafluoroantimonate
4-methylphenyl-4-isopropylphenyliodonium tetrakis(pentafluorophenyl)borate Reducing agents for carrying out the redox reaction for formation of acids are organic or inorganic compounds or polymers which are capable of lowering the charge of the heteroatom within the diaryliodonium salt. Compounds which are worth mentioning are ascorbic acid and derivatives thereof, in particular the palmitate, oleate and acetate. Tin(II) compounds can also be employed, for example $Sn^{2+}$ carboxylates, in particular tin octoate, tin stearate, tin laurate, tin citrate, tin oxalate and tin benzoate. Among the organic compounds there may be mentioned α-hydroxy compounds, for example ketones, in particular acyloins and benzoins. Also included are iron(II) compounds, for example ferrocenes, $FeBr_2$ and $FeCl_2$, reducing sugars, such as glucose, fructose and galactose, phenols, such as thiophenol, silanes and organosiloxanes.

Copper compounds are to be understood as meaning copper(I) and copper(II) compounds, for example salts of carboxylic acids and mineral acids, such as CuBr, CuCl, Cu(II) benzoate, Cu(II) citrate, Cu(II) formate, Cu(II) acetate, Cu(II) stearate, Cu(II) oleate, Cu(II) carbonate, Cu(II) gluconate, Cu(II) naphthenoate or Cu(II) acetylacetonate.

Copper chelates such as are mentioned in Cotton and Wilkinson, Advanced Inorganic Chemistry, 3rd Edition, Interscience Publishers, New York, 1972, pages 905 to 922 can also be used. Preferred copper chelates are those which can be incorporated or dispersed in the cationically polymerizable material in a sufficient amount. Copper acetylacetonate, copper salicylate, $CuI(C_6H_5)_3P$, CuI $(C_2H_5O)_3P$, $CuCl_2C_2H_8N_2$, $[(N—C_4H_9)_4N]_2CuCl_4$ etc. are particularly suitable.

Alkyl halides which are suitable for the dehalogenation of alkyl halides assisted by metal salts are described in "Makromol. Chem." 178, 2139–2140 (1977) and in "Die Makromolekulare Chemie" 156 (1972) 325–328.

Compounds of the type $R_3C—X$, wherein X represents a halogen, preferably Cl and Br, and R represents any desired substituted or unsubstituted aliphatic or cycloaliphatic radical with a chain length of 1 to 15 C atoms, preferably 1 to 8 C atoms, or an aromatic radical substituted in any desired manner, are suitable in particular. Compounds with up to three different substituents on the central C atom can also be used.

Metal salts are understood as meaning inorganic or organic metal salts which are capable of abstracting the halogen from the compounds of the abovementioned type. Possible salts are those such as $AgBF_4$, $Ag\ SbF_6$, $AlCl_3$, $ZnCl_2$ and also $BF_3$. Lewis acid compounds of the type $M(III)X_3$, $M(II)X_2$, $M(V)X_5$ and possible adducts thereof with AgX are generally suitable. X here represents a halogen, preferably F, Cl or Br, and M represents a metal from the main or sub-group in question, preferably from main groups III and V, and in these preferably B, Al, Sb or As, and from sub-groups I, II, IVa and VIIIa, and in these preferably Cu, Ag, Zn, Fe, Co, Ni and Ti.

Diluents as flow improvers as constituent (C) are present in at least one of the two components of the preparations according to the invention. Diluents which are usually used as plasticizers can advantageously be employed.

Typical representatives are the esters of phthalic acid, such as di-2-ethylhexyl phthalate, or the esters of polybasic aliphatic acids, such as dioctyl adipate or acetyl tributylcitrate.

In addition, aliphatic and aromatic hydrocarbons with 6 to 30 C atoms which can be branched or unbranched are very suitable. Typical examples are polypropylene oils or polyisobutylene oils. Advantageously, aromatic hydrocarbons such as polyphenylene compounds, dibenzyltoluene and dibenzylphenyl methane are used.

Polyester polyols which can be prepared for example by polycondensation from low-molecular polyols and polycarboxylic acids and/or their anhydrides can also be used.

Typical representatives of this class are marketed by Hüls under the name Dynacoll. Preferably, polyester polyols whose molar masses are between 1000 and 5000 g/mol and hydroxyl equivalent masses of 500 to 2000 are used.

Particularly preferably, polyester polyols as they can be obtained through catalysed reactions of caprolactone with different starting alcohols can be used.

Typical representatives of this compound class are marketed by UCC under the name Tone or by Daicel under the name Placcel.

Polycaprolactone triols with molar masses of 200 to 1000 g/mol and polycaprolactone diols with molar masses of 300 to 2000 g/mol can be used.

Furthermore, polycarbonate diols with molar masses of 400 to 2000 g/mol and the general structure

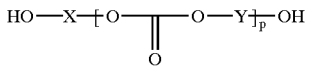

can be used as diluents, X and Y being able to be identical or different and, independently of each other, mean alkylene, arylene, alkarylene, polyoxyalkylene and p can assume values between 1 and 50.

Furthermore, partly epoxidated polybutane diols can optionally be used which represent homopolymerisates of butadiene, which are terminated with OH groups, have molar masses of 1000 to 5000 g/mol and possess a high content of double bonds, which, through epoxidation, can optionally be partly converted to central aliphatic epoxide groups. Representatives of this compound class are marketed by Atochem under the name "Poly bd".

Finally, polyether polyols of the general structure:

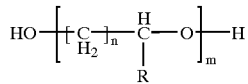

can also be used, m meaning an integer of 20 to 150, n an integer of 1 to 5 and R hydrogen or C1–C4 alkyl.

Preferably, mixed polyether polyols which are composed of propylene oxide units and/or ethylene oxide units and/or tetrahydrofurane units, are used.

Alkoxy-extended polyols such as for example ethoxylated Bisphenol A or propoxylated trimethylol propane can also advantageously be used.

To adjust the properties, it can be expedient to use mixtures of polyols of different average molar mass and different structure.

By modifiers are meant for example fillers. Fillers can be for example quartz, quartz powder, ground or reactive glasses, fragment polymerisates, silica gels as well as pyrogenic silicic acid or their granules, customary in the dental field. But other fillers such as for example finely-distributed metal or plastic powder, barium sulphate, titanium dioxide or in general finely-ground minerals are suitable. For better incorporation into the polymer matrix, it can be advantageous to hydrophobize the fillers. Hydrophobizing agents are silanes, for example glycidyloxypropyltrimethoxysilane. The maximum particle size of the inorganic fillers is 100 μm, preferably 20 μm.

As further modifiers, such as dyes or thixotropic agents, the substances customary in the dental engineering field can be used.

The two components of the preparations according to the invention can be stored separately, for example in double-chamber cartridges, and be mixed internally before use by eduction via a static or dynamic mixer. Hand-mixing variants are also possible.

The ratio between the component containing no epoxy compounds and the component containing epoxy compounds can be 1:10 to 1:1 and preferably 1:5 to 1:2.

EXAMPLES

The invention is described in more detail below by examples from the model material sector, which are in no case intended to limit the scope of the invention. The substances used in the course of these examples can be obtained from the following manufacturers:

| | |
|---|---|
| Aerosil R 805 | Degussa |
| Aerosil R202 | Degussa |
| Celloxide 2021 P | UCB |
| Citrofol B1 | Jungbunzlauer |
| Dianol 265 | Akzo Nobel |
| Jarytherm DBT | Elf Atochem |
| Placcel 305 | Interorgana(Daiccel) |
| Rhodorsil 2074 | Rhone-Poulenc |
| Silbond FW 100 EST | Quarzwerke Frechen |
| Silbond FW 300 EST | Quarzwerke Frechen |
| Silbond FW 600 EST | Quarzwerke Frechen |
| Titanium dioxide P 25 | Degussa |

The substance CEPK is a cycloaliphatic epoxy resin with four epoxy groups prepared in accordance with the instructions of DE-A-196 48 283.

The substance LM used as a stabilizer was prepared in accordance with DE-A-197 53 461, example 1.

The base pastes and catalyst pastes characterized in the following examples with the aid of their compositions were prepared in 3-finger kneaders on a 100 g scale. After achieving a homogeneous state of mixing, the pastes were evacuated and then introduced into 4:1 double-chamber cartridges.

Comparison Example 1

| Base paste | | Catalyst paste | |
|---|---|---|---|
| Celloxide 2021 P | 49.899% | Dianol 265 | 77.00% |
| Silbond FW 600 EST | 49.000% | Silbond FW 300 EST | 20.00% |
| Aerosil R202 | 1.000% | Aerosil R202 | 1.00% |
| LM | 0.101% | Titanium dioxide P 25 | 1.00% |
| | | HSbF$_6$ 60% | 1.00% |

Example 1

| Base paste | | Catalyst paste | |
|---|---|---|---|
| Silbond FW 100 EST | 46.979% | Silbond FW 100 EST | 46.944% |
| CEPK | 16.992% | Dianol 265 | 19.477% |
| Silbond FW 600 EST | 15.993% | Silbond FW 600 EST | 15.981% |
| Celloxide 2021 P | 8.996% | Butyl lactate | 8.490% |
| Poly-THF 250 | 4.498% | Rhodorsil 2074 | 5.528% |
| Dianol 265 | 3.998% | Aerosil R805 | 1.498% |
| Aerosil R805 | 1.500% | Ascorbic acid | 0.984% |
| Copper naphthenoate 8% in white spirit | 0.544% | HSbF$_6$ 60% | 0.599% |
| Titanium dioxide P25 | 0.500% | Titanium dioxide P 25 | 0.499% |

Example 2

| Base paste | | Catalyst paste | |
|---|---|---|---|
| Silbond FW 100 EST | 31.750% | Silbond FW 100 EST | 62.500% |
| Silbond FW 600 EST | 31.750% | Dianol 265 | 13.065% |
| CEPK | 17.300% | Butyl lactate | 8.500% |
| Celloxide 2021 P | 10.315% | Poly-THF 250 | 6.915% |
| Dianol 265 | 4.570% | Rhodorsil 2074 | 5.535% |
| Poly-THF 250 | 2.418% | Aerosil R805 | 1.500% |
| Aerosil R805 | 1.500% | Titanium dioxide P 25 | 1.000% |
| Copper dimethacrylate | 0.397% | Ascorbic acid | 0.985% |

Example 3

| Base paste | | Catalyst paste | |
|---|---|---|---|
| Silbond FW 100 EST | 47.845% | Silbond FW 100 EST | 43.713% |
| Silbond FW 600 EST | 14.952% | Placcel 305 | 31.009% |
| CEPK | 12.460% | Silbond FW 600 EST | 15.005% |
| Celloxide 2021 P | 12.460% | Copper tetrafluoroborate | 4.272% |
| Placcel 305 | 4.485% | Jarytherm DBT | 4.001% |
| Jarytherm DBT | 3.987% | Aerosil R805 | 1.500% |
| Diphenylmethyl chloride | 1.818% | Titanium dioxide P 25 | 0.500% |
| Aerosil R805 | 1.495% | | |
| Titanium dioxide P 25 | 0.498% | | |

Example 4

| Base paste | | Catalyst paste | |
|---|---|---|---|
| Silbond FW 100 EST | 47.025% | Silbond FW 100 EST | 41.943% |
| Silbond FW 600 EST | 14.976% | Dianol 265 | 18.475% |
| CEPK | 10.483% | Silbond FW 600 EST | 14.980% |
| Celloxide 2021 P | 10.483% | Placcel 305 | 10.985% |
| Dianol 265 | 6.490% | Iron(II) tetrafluoroborate | 6.068% |
| Citrofol B1 | 5.990% | Citrofol B1 | 4.993% |
| Triphenylmethyl chloride | 2.556% | Aerosil R805 | 1.498% |
| Aerosil R805 | 1.498% | Tetrafluoroboric acid 48% | 0.559% |
| Titanium dioxide P 25 | 0.499% | Titanium dioxide P 25 | 0.499% |

Example 5

| Base paste | | Catalyst paste | |
|---|---|---|---|
| Silbond FW 100 EST | 45.804% | Silbond FW 100 EST | 44.432% |
| CEPK | 16.589% | Placcel 305 | 26.991% |
| Silbond FW 600 EST | 14.990% | Silbond FW 600 EST | 14.996% |
| Celloxide 2021 P | 7.993% | Jarytherm DBT | 7.997% |
| Jarytherm DBT | 5.996% | Zinc tetrafluoroborate | 3.584% |
| Placcel 305 | 4.497% | Aerosil R805 | 1.500% |
| Triphenylmethyl chloride | 2.132% | Titanium dioxide P 25 | 0.500% |
| Aerosil R805 | 1.499% | | |
| Titanium dioxide P 25 | 0.500% | | |

The comparison of the properties of the materials according to the invention with commercially available products in table 1 clearly shows that the materials offer advantages to the dental technician.

| Material | Millable after [min] | Flexural strength [Mpa] | Can be mixed automatically |
|---|---|---|---|
| Comparison example 1 | 30 | 105 ± 14 | Yes |
| Example 1 | 45 | 65 ± 6 | Yes |
| Example 2 | 45 | 99 ± 7 | Yes |
| Example 3 | 30 | 62 ± 5 | Yes |
| Example 4 | 45 | 34 ± 3 | Yes |
| Example 5 | 45 | 41 ± 1 | Yes |
| Comparison example 2 | 30–60 | 16 ± 2 | No |
| Comparison example 3 | 360–480 | 43 ± 2 | No |

In comparison example 1, in which only free acid was employed as the initiator, the processing time of 60 seconds was too short. A super-hard gypsum of the Fujirock (GC) brand is used as comparison example 2, and a conventionally curing epoxy resin of the Blue Star type E (Girbach) brand is used as comparison example 3.

What is claimed is:

1. Two-component preparation comprising components (I) and (II), wherein at least one component comprises epoxy compounds and the preparation cures by cationic polymerization, initiated by Lewis and/or Brönsted acids, after mixing of the two components, the preparation comprising the Lewis and/or Brönsted acids in the form of precursor compounds which are suitable for the formation of Lewis and/or Brönsted acids and are formed by chemical reaction after mixing of the two components.

2. Preparation according to claim 1, characterized in that the epoxy compounds and the compounds which are capable of the formation of Lewis and/or Brönsted acids and do not react with the epoxy compounds are present in component (I) and/or in component (II) in any desired distribution.

3. Preparation according to claim 1, characterized in that it additionally comprises Lewis and/or Brönsted acids in free form as part of that component which comprises no epoxy compounds.

4. Preparation according to claim 3, characterized in that the epoxy compounds are present in component (I), the Lewis and/or Brönsted acids in free form are present in component (II) and the compounds which are suitable for the formation of Lewis and/or Brönsted acids and do not react with the epoxy compounds are present in component (I) and/or (II) in any desired distribution.

5. Dental composition from preparations according to one of claims 1 to 4, characterized in that they comprise, distributed over components (I) and (II), the constituents:
   (A) 10 to 80 wt. % of epoxy compounds,
   (B) 0.01 to 20 wt. % of compounds which are capable of the formation of Lewis and/or Brönsted acids, and optionally free Lewis and/or Brönsted acids,
   (C) 10 to 89.99 wt. % of diluents,
   (D) 0 to 79.99 wt. % of modifiers,
   the wt. % data relating to the total weight of the mixed preparations.

6. Dental composition according to claim 5, characterized in that cycloaliphatic epoxy compounds and/or aromatic epoxy compounds and/or aliphatic epoxy compounds are used as constituent (A).

7. Dental composition according to claim 5, characterized in that cycloaliphatic epoxy compounds with at least two epoxy groups or cycloaliphatic epoxy compounds with at least four epoxy groups or cycloaliphatic epoxy compounds with two epoxy groups and cycloaliphatic epoxy compounds with at least four epoxy groups are used as constituent (A).

8. Dental composition according to claim 5, characterized in that the content of epoxy compounds with at least four epoxy groups in the mixed preparations is 5 to 60 wt. %, preferably 5 to 50 wt. %.

9. Dental composition according to claim 5, characterized in that it comprises compounds which are suitable for the formation of Brönsted acids, and in that these are present in an amount such that the concentration of the Brönsted acid optionally employed in free form is 0.1 to 5 wt. %, based on the mixed dental composition.

10. Dental composition according to claim 9, characterized in that the Brönsted acids are produced by a redox reaction from bisaryliodonium salts, and that free Brönsted acids are optionally additionally present.

11. Dental composition according to claim 10, characterized in that the free Brönsted acids optionally additionally present and the Brönsted acids produced by redox reactions from bisaryliodonium salts are identical, or in that the free Brönsted acids optionally additionally present and the Brönsted acids produced by redox reactions from bisaryliodonium salts are different.

12. Dental composition according to claim 5, characterized in that the Brönsted acid or Lewis acid carbenium ions are produced by reaction of alkyl or aryl or mixed alkylaryl halides with metal salts after mixing of the two components.

13. Dental composition according to claim 12, characterized in that zinc, iron and/or copper salts are employed as the metal salts.

14. Dental composition according to claim 5, characterized in that the anion of the Brönsted acids is chosen from the group consisting of hexafluorophosphate, hexafluoroarsenate, hexafluoroarntimonate, tetrakis (pentafluorophenyl)borate and tetrafluoroborate.

15. Dental composition according to claim 5, characterized in that the ratio between the component comprising no epoxy compounds and the component comprising epoxy compounds 1:10 to 1:1, and preferably 1:5 to 1:2.

16. Process for mixing the dental composition according to claim 5, characterized in that mixing of the two components takes place by dynamic mixing processes or with the air of a static mixer mounted on a double-chamber cartridge.

17. A dental composition made by the preparations according to any one of claims 1 to 4.

18. A dental composition which comprises epoxy compounds wherein said dental composition cures by cationic polymerization initiated by a Lewis and/or a Brönsted acid and wherein the Lewis and/or the Brönsted acid are employed in the form of precursor compounds which are suitable for the formation of the Lewis and/or the Brönsted acid and are formed by chemical reaction during or after mixing the dental composition.

19. Dental models, fillings, temporary crowns, temporary bridges or fixing cements made by the dental composition according to claim 18.

20. Dental models, fillings, temporary crowns or bridges of cement made by the dental composition according to claim 17.

* * * * *

UNITED STATES PATENT AND TRADEMARK OFFICE
CERTIFICATE OF CORRECTION

PATENT NO.    : 6,613,437 B1
DATED         : September 2, 2003
INVENTOR(S)   : Eckhardt, Gunther et al.

It is certified that error appears in the above-identified patent and that said Letters Patent is hereby corrected as shown below:

<u>Column 6,</u>
Line 12, delete "IIII" and insert -- III --, therefor.

<u>Column 7,</u>
Line 40, delete "Ag SbF$_6$" and insert -- AgSbF$_6$ --, therefor.

Signed and Sealed this

Sixth Day of September, 2005

JON W. DUDAS
*Director of the United States Patent and Trademark Office*